United States Patent [19]

Mueller

[11] 4,336,252

[45] Jun. 22, 1982

[54] 1-CYCLOALKYL PHOSPHONIUM SALTS

[75] Inventor: Richard A. Mueller, Glencoe, Ill.

[73] Assignee: G. D. Searle & Co., Skokie, Ill.

[21] Appl. No.: 175,790

[22] Filed: Aug. 6, 1980

[51] Int. Cl.³ .................. A01N 9/36; A61K 31/66; A61L 13/00; C07F 9/54
[52] U.S. Cl. ................................................ 424/198
[58] Field of Search .............. 424/198, 211, 212, 217; 568/11, 9

[56] References Cited

U.S. PATENT DOCUMENTS 3,654,372 4/1972 Birum et al. .................. 424/198
4,049,669 9/1977 Lam et al. ..................... 568/9
4,075,407 2/1978 Mueller ......................... 424/203

Primary Examiner—H. M. S. Sneed
Attorney, Agent, or Firm—W. Dennis Drehkoff; Albert Tockman

[57] ABSTRACT

1-Cycloalkyl phosphonium salts represented by the formula

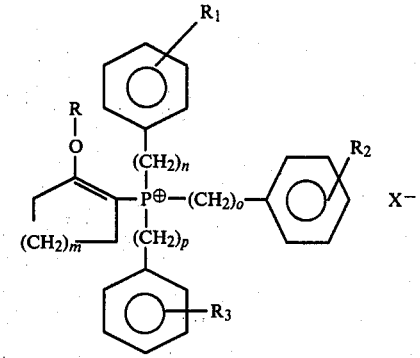

wherein: R is selected from the group consisting of lower alkyl, hydroxy lower alkyl, halo lower alkyl, amino lower alkyl, cyano lower alkyl, lower alkenyl with the limitation that the double bond is not on the carbon atom attached to the oxygen atom, benzyl, substituted benzyl and

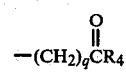

wherein q is 0 or 1 and $R_4$ is selected from the group consisting of hydroxy, loweralkoxy, phenyl, substituted phenyl, and

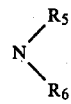

wherein $R_5$ and $R_6$ are the same or different members of the group consisting of hydrogen and loweralkyl or taken together form a 5 or 6 membered ring; m is 1, 2 or 3; n is 0 or 1; o is 0 or 1; p is 0 or 1; $R_1$, $R_2$ and $R_3$ are the same or different members of the group consisting of hydrogen, lower alkyl, lower alkoxy and halo; and X is a pharmaceutically acceptable anion. The compounds are useful as analgesic agents.

34 Claims, No Drawings

1-CYCLOALKYL PHOSPHONIUM SALTS

BACKGROUND OF THE INVENTION

While there are a number of commercially available mild to moderate analgesic agents, the search for alternative analgesic agents has continued because of the problems attendant with current therapy.

Aspirin and related salicylates are considered to be non-narcotic analgesic agents useful for relieving mild to moderate pain, in addition to their anti-inflammatory and anti-pyretic properties. However, the ingestion of salicylic acid or related salycilates may result in epigastric distress, nausea and vomiting. This widely used class of non-narcotic analgesic agents may also cause gastric ulceration and even hemorrhage both in experimental animals and man. Exacerbation of peptic ulcer symptoms and erosive gastritis have all been reported in patients on high dose therapy, i.e., arthritis patients. Aspirin is also one of the most common causes of drug poisoning in young children and has a potential of serious toxicity if used improperly.

Acetominophen is also considered to be a non-narcotic analgesic agent useful in treating pain associated with simple headache, common muscular aches, etc. While acetominophin is particularly useful for patients who cannot take aspirin, i.e. ulcer patients, its use in contraindicated in individuals who have exhibited a sensitivity to it.

In addition to their drawbacks in view of their potential side effects, the mild, non-narcotic analgesic agents are not sufficiently potent to relieve the severe pain associated with surgery, cancer and the like.

Unfortunately, the potent analgesic agents capable of relieving such severe pain are also narcotic agents and their use entails the risk of producing physical or psychological dependence.

One moderate analgesic agent which has enjoyed great commercial success for a number of years, α-d-propoxyphene hydrochloride (Darvon ®, Eli Lilly and Co., Indianapolis, Ind.) has been widely used to relieve pain associated with dental extractions, afterbirth pain, and some post-operative pain. This widely used analgesic agent has been reported to be ineffective in relieving many types of pain, and recently, reports of serious side effects and deaths have created a need for alternative, moderate analgesic agents. The present invention provides such agents.

SUMMARY OF THE INVENTION

The analgesic agents of the present invention are novel 1-cycloalkyl phosphonium salts represented by the formula:

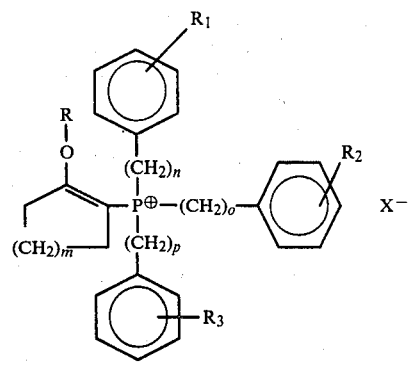

wherein: R is selected from the group consisting of lower alkyl, hydroxy lower alkyl, halo lower alkyl, amino lower alkyl, cyano lower alkyl, lower alkenyl with the limitation that the double bond is not on the carbon atom attached to the oxygen atom, benzyl, substituted benzyl and

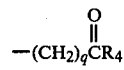

wherein q is 0 or 1 and $R_4$ is selected from the group consisting of hydroxy, loweralkoxy, phenyl, substituted phenyl, and

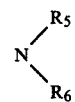

wherein $R_5$ and $R_6$ are the same or different members of the group consisting of hydrogen and loweralkyl or taken together form a 5 or 6 membered ring; m is 1,2 or 3; n is 0 or 1; o is 0 or 1; p is 0 or 1; $R_1$, $R_2$ and $R_3$ are the same or different members of the group consisting of hydrogen, lower alkyl, lower alkoxy and halo; and X is a pharmaceutically acceptable anion.

The compounds of this invention are useful as analgesic agents when administered to mammalian patients suffering from mild to moderate pain in oral or patenteral dosages of from about 0.2 to 20 mg/kg of body weight and preferably from about 1 to 10 mg/kg of body weight. Generally the compounds are administered every three to six hours unless formulated in sustained release form, in which case they may be administered every 6 to 12 hours until the pain has diminished.

DETAILED DESCRIPTION OF PREFERRED EMBODIMENTS

The term "lower alkyl", as used herein, refers to straight and branched chain alkyl radicals having from 1 to 6 carbon atoms such as methyl, ethyl, n-propyl, iso-propyl, n-butyl, iso-butyl, tert-butyl, n-pentyl, 2-methyl-butyl, 2,2-dimethyl-propyl, n-hexyl, etc.

The terms "hydroxy lower alkyl", "halo lower alkyl", "amino lower alkyl", and "cyano lower alkyl" refer to substituted $C_2$–$C_6$ straight or branched chain alkyl radicals such as hydroxyethyl, 3-cyano-n-pentyl, 2-chloro-n-propyl; trifluoromethyl, etc., i.e., mono, di- or tri-substituted lower alkyl radicals.

The term "lower alkenyl" refers to $C_2$–$C_6$ straight or branched chain alkenyl radicals and are limited to those having a double bond in a position other than on the carbon adjacent the oxygen.

The term "substituted benzyl" refers to a mono, di- or tri-substituted benzyl radical, substituted by lower alkyl, lower alkoxy, halo, nitro, cyano, halo lower alkyl, hydroxy, alkylcarbonyl, etc.

The term "lower alkoxy" refers to straight or branched chain $C_1$-$C_6$ alkoxy groups, i.e., methoxy, ethoxy, iso-propoxy, etc.

The term "anions" includes, but is not limited to pharmaceutically acceptable (non-toxic) anions such as chloride, bromide, iodide, fluoride, acetate, propionate, sulfate, bisulfate, acetate, oxalate, valerate, oleate, laurate, borate, citrate, maleate, fumarate, lactate, succinate, tartrate, benzoate, tetrafluoroborate, trifluoromethylsulfonate, napsylate, tosylate, etc.

The term "pharmaceutically acceptable salts" refers to the hydrochlorides, hydrobromides, acetates etc. as well as the inner salts.

The analgesic activity of the compounds of the present invention was initially established in the mouse writhing test.

The Wittig reagents used as starting materials to prepare the compounds of this invention can be prepared by the 5 step process of House, H. O. et al., J. Org. Chem. 28, 90(1963) from the appropriate lactone, or, in the case of the α-ketocyclohexyl starting materials, from the improved process of one aspect of the present invention.

Alkylation or acylation of these activated ylides on oxygen is aided by steric hinderance, the choice of non-protic solvents (although alkylation is possible in protic solvents) and the fact that an ylide is an internally charge compensated anion, therefore association with external cations is precluded. The use of non-polar, aprotic solvents also facilitate product isolation due to the polarity of the products.

Generally, the starting ylides are sufficiently reactive that reaction usually occurs conveniently at room temperature although higher or lower temperatures can be used if desired.

The process aspect of this invention allows the synthesis of α-ketocyclohexylidene triphenyl phosphorane in one step from the compounds of commonly assigned U.S. Pat. No. 4,075,407 or a total of three steps from a lactone disclosed in commonly assigned, copending U.S. Ser. No. 172,781, filed July 28, 1980, thus affording a considerable savings over prior art processes.

The following examples further illustrate the present invention.

EXAMPLE 1

Preparation of [2-(phenylmethoxy)-1-cyclohexen-1-yl]triphenylphosphonium bromide Three grams of α-ketocyclohexylidenetriphenylphosphorane [J. Org. Chem., 28, pp 90–92(1963)] is suspended in 50 ml of acetone and 1.0 ml of benzyl bromide (1.1 eq) is added. The reaction mixture is stirred at room temperature under argon for one day, heated at reflux for one day, then filtered. The filtrate is washed twice with acetone and dried at 60° C./0.5 mm pressure for one day to provide 3.48 g of the desired product, m.p. 206°–208° C. and having the formula:

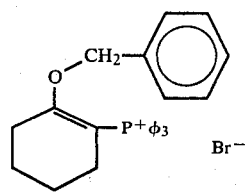

EXAMPLE 2

Preparation of [2-(1-methylethoxy)-1-cyclohexen-1-yl]triphenylphosphonium iodide Two grams of α-ketocyclohexylidenetriphenylphosphorane is suspended in about 50 ml of acetone and 20 ml of chloroform and heated at reflux under argon for one day. The solution is cooled to room temperature, the solvents removed with a rotary evaporator and the resulting product triturated with acetone, filtered and dried overnight at 60° C./0.5 mm pressure to yield 1.2 g of product, m.p. 216°–219° C. and having the formula:

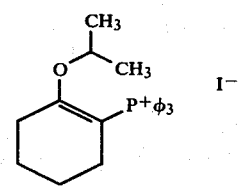

EXAMPLE 3

Preparation of (2-methoxy-1-cyclohexen-1-yl)triphenylphosphonium, 4-methylbenzenesulfonate α-Ketocyclohexylidenetriphenylphosphorane (1.3 g) is suspended in about 50 ml of xylene and 1.1 mg of methyl tosylate is added thereto, all under argon. The reaction mixture is refluxed under argon for about 1 day, cooled to room temperature, the xylene decanted and the resulting oil washed twice with toluene. The oil is crystallized and recrystallized from ether/acetone to yield the desired product having the following analyses and formula:

Analysis Calcd. for $C_{32}H_{33}O_4PS$: C, 70.57; H, 6.11; P, 5.69. Found: C, 70.26; H, 6.17; P, 5.65.

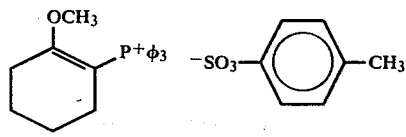

EXAMPLE 4

Preparation of [2-(3-methyl-2-butenyloxy)-1-cyclohexen-1-yl]triphenylphosphonium bromide α-Ketocyclohexylidenetriphenylphosphorane (2.0 g) is suspended in 50 ml of acetone and 830 mg of 1-bromo-3-methyl-2-butene is added thereto, all under a nitrogen atmosphere. The reaction mixture is stirred at room temperature for about 10 days and filtered. The crystals are washed with acetone three times, and dried at 55°

C./0.5 mm pressure for about two hours to yield the desired product having the formula:

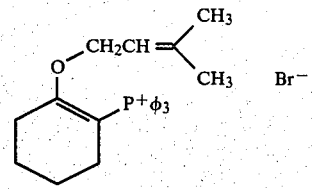

Analysis Calcd. for $C_{29}H_{32}BrOP$: C, 68.64; H, 6.36; P, 6.10. Found: C, 68.30; H, 6.42; P, 5.84.

EXAMPLE 5

Preparation of [2-(2-oxo-2-phenylethoxy)-1-cyclohexen-1-yl]triphenylphosphonium bromide α-Ketocyclohexylidenetriphenylphosphorane (2.0 g) and phenacyl bromide are reacted following the method of Example 4 to provide 2.1 g of the desired product, m.p. 182.5°–185° C., having the formula

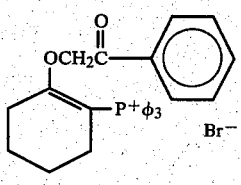

EXAMPLE 6

Preparation of [2-(((2-carboxyphenyl)-carbonyl)oxy)-1-cyclohexen-1-yl]triphenylphosphonium hydroxide, inner salt α-Ketocyclohexylidenetriphenylphosphorane (2.0 g) is dissolved/suspended in 50 ml of acetone and 850 mg of phthalic anhydride is added thereto, all under a nitrogen atmosphere. The reaction mixture is stirred at room temperature for 4 days, after which the solvent is removed under a nitrogen stream and the resulting oil crystallized from acetone to give 1.7 g of the inner salt having the formula

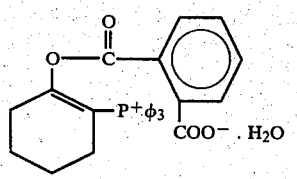

Analysis Calc. for $C_{32}H_{29}O_5P$: C, 73.27; H, 5.53; P, 5.91. Found: C, 73.01; H, 5.53; P, 5.99.

The inner salt can be conveniently converted, if desired, to a pharmaceutically acceptable anionic salt, by treatment with acid.

EXAMPLE 7

Preparation of [2-(2-methoxy-2-oxoethoxy)-1-cyclohexen-1-yl]triphenylphosphonium bromide α-Ketocyclohexylidenetriphenylphosphorane (2.0 g) and 0.5 ml of methylbromoacetate are reacted following the method of Example 4 to provide the desired product having the formula

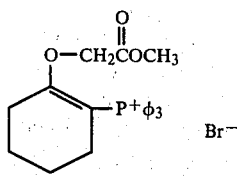

Analysis Calcd. for $C_{27}H_{28}BrO_3P$ $0.25H_2O$: C, 62.85; H, 5.57; P, 6.01. Found: C, 62.81; H, 5.45; P, 5.94.

EXAMPLE 8

Preparation of [2-(phenylmethoxy)-1-cyclopenten)1-yl]triphenylphosphonium bromide

[2-(Phenylmethoxy)-1-cyclopenten-1-yl]triphenylphosphonium bromide is prepared by the method of Example 1 from α-ketocyclopentylidenetriphenylphosphorane.

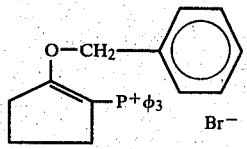

EXAMPLE 9

Preparation of [2-(phenylmethoxy)-1-cyclohepten-1-yl]triphenylphosphonium bromide

[2-(Phenylmethoxy)-1-cyclohepten-1-yl]triphenylphosphonium bromide is prepared by the method of Example 1 from α-ketocycloheptylidenetriphenylphosphorane.

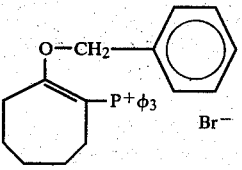

EXAMPLE 10

Preparation of [2-(1-methylethoxy)-1-cyclopenten-1-yl]triphenylphosphonium iodide

[2-(1-methylethoxy)-1-cyclopenten-1-yl]triphenylphosphonium iodide is prepared by the method of Example 2 from α-ketocyclopentylidenetriphenylphosphorane.

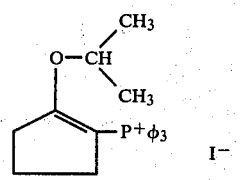

EXAMPLE 11

Preparation of
[2-(1-methylethoxy)-1-cyclohepten-1-yl]triphenylphosphonium iodide

[2-(1-Methylethoxy)-1-cyclohepten-1-yl]triphenylphosphonium iodide is prepared by the method of Example 2 from α-ketocycloheptylidenetriphenylphosphorane.

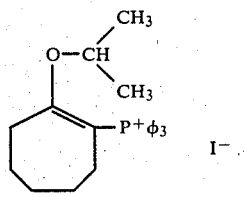

EXAMPLE 12

Preparation of
(2-methoxy-1-cyclopenten-1-yl)triphenylphosphonium 4-methylbenzenesulfonate 2-Methoxy-1-cyclopenten-1-yl)triphenylphosphonium 4-methylbenzenesulfonate is prepared by the method of Example 3 from α-ketocyclopentylidenetriphenylphosphorane.

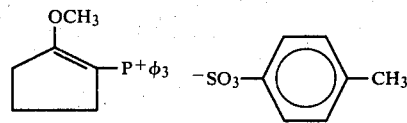

EXAMPLE 13

Preparation of
(2-methoxy-1-cyclohepten-1-yl)diphenyl-2-o-methylphenylphosphonium 4-methylbenzensulfonate 2-Methoxy-1-cyclohepten-1-yl)diphenyl-2-o-methylphenyltriphosphonium 4-methylbenzenesulfonate is prepared by the method of Example 3 from α-ketocycloheptylidenediphenyl-2-o-methylphenylphosphorane.

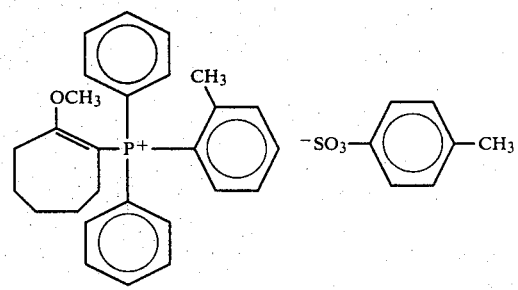

EXAMPLE 14

Preparation of
[2-(3-methyl-2-butenyloxy)-1-cyclopenten-1-yl]triphenylphosphonium bromide

[2-(3-Methyl-2-butenyloxy)-1-cyclo-penten-1-yl]triphenylphosphonium bromide is prepared by the method of Example 4 from α-ketocyclopentylidenetriphenylphosphorane.

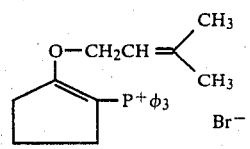

EXAMPLE 15

Preparation of
[2-(3-methyl-2-butenyloxy)-1-cyclohepten-1-yl]triphenylphosphonium bromide

[2-(3-Methyl-2-butenyloxy)-1-cyclohepten-1-yl]triphenylphosphonium bromide is prepared by the method of Example 4 from α-ketocycloheptylidenetriphenylphosphorane.

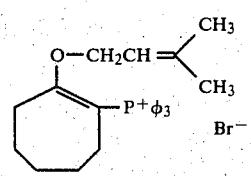

EXAMPLE 16

Preparation of
[2-(2-oxo-phenylethoxy)-1-cyclopenten-1-yl]triphenylphosphonium bromide

[2-(2-oxo-phenylethoxy)-1-cyclopenten-1-yl]triphenylphosphonium bromide is prepared by the method of Example 5 from α-ketocyclopentylidenetriphenylphosphorane.

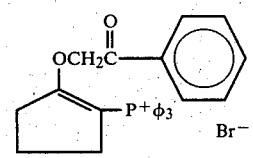

EXAMPLE 17

Preparation of
[2-(2-oxo-phenylethoxy)-1-cyclohepten-1-yl]triphenylphosphonium bromide

[2-(2-Oxo-phenylethoxy)-1-cyclohepten-1-yl]triphenylphosphonium bromide is prepared by the method of Example 5 from α-ketocycloheptylidenetriphenylphosphorane.

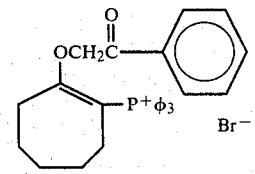

EXAMPLE 18

Preparation of
[2-(((2-carboxyphenyl)carbonyl)oxy)-1-cyclopenten-1-yl]triphenylphosphonium hydroxide, inner salt, is prepared by the method of Example 6 from α-ketocyclopentylidenetriphenylphosphorane.

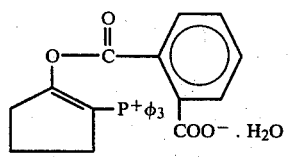

EXAMPLE 19

Preparation of
[2-(((2-carboxyphenyl)carbonyl)oxy)-1-cyclohepten-1-yl]triphenylphosphonium hydroxide, inner salt

[2-(((2-Carboxyphenyl)carbonyl)oxy]-1-cyclohepten-1-yl]triphenylphosphonium hydroxide, inner salt is prepared by the method of Example 6 from α-ketocycloheptylidenetriphenylphosphorane.

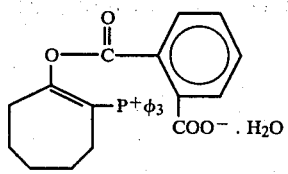

EXAMPLE 20

Preparation of
[2-(2-methoxy-2-oxoethoxy)-1-cyclopenten-1-yl]triphenylphosphonium bromide

[2-(2-Methoxy-2-oxoethoxy)-1-cyclopenten-1-yl]triphenylphosphonium bromide is prepared by the method of Example 7 from α-ketocyclopentylidenetriphenylphosphorane.

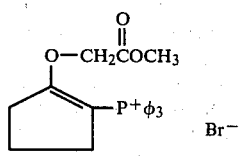

EXAMPLE 21

Preparation of
[2-(2-methoxy-2-oxoethoxy)-1-cyclohepten-1-yl]triphenylphosphonium bromide

[2-(2-Methoxy-2-oxoethoxy)-1-cyclohepten-1-yl]triphenylphosphonium bromide is prepared by the method of Example 7 from α-ketocycloheptylidenetriphenylphosphorane.

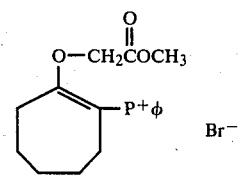

It will be apparent to those skilled in the art that by starting with the appropriately substituted α-ketocycloalkylidenetriphenyl or benzyl or substituted phenyl or benzylphosphorane, the desired product is obtained, i.e.

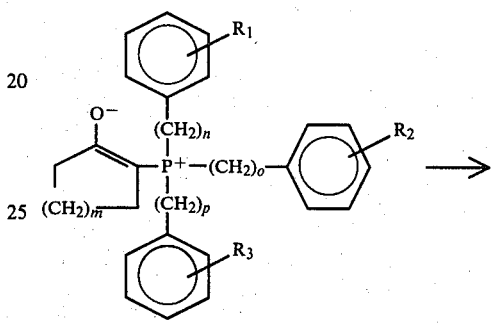

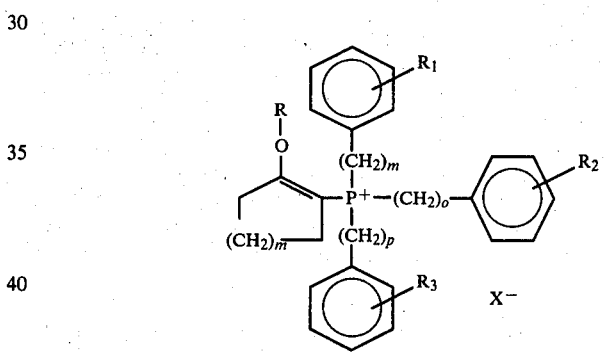

wherein R, $R_1$, $R_2$, $R_3$, m, n, o and p are as defined above.

The following examples illustrate the improved process of the present invention.

EXAMPLE 22

Preparation of
α-ketocyclohexylidenetriphenylphosphonium bromide

[(Tetrahydro-2H-pyran-2-ylidene)methyl]triphenylphosphonium chloride (U.S. Pat. No. 4,075,407) was suspended in xylene under argon and refluxed with vigorous stirring for 6 days. The reaction mixture was cooled to room temperature, filtered, stirred with acetone for two hours, filtered and dried overnight at 50° C. to give 30 g of product, m.p. 236°–240° C.

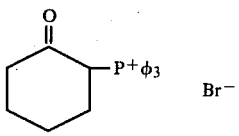

EXAMPLE 23

Conversion of α-ketocyclohexylidenetriphenylphosphonium bromide to α-ketocyclohexylidenetriphenylphosphorane 8.5 g of the product of Example 2, was dissolved in about 50 ml of methanol and 450 ml of H$_2$O was added. Solid potassium carbonate (excess) was added and the crystals filtered, washed with water and dried overnight at 110° C./0.5 mm pressure to give 6.88 g of product.

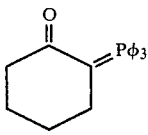

While the phosphorane of Example 23 can be prepared in a single step by adding base to Example 22, it is advantageous to add any suitable base such as triethylamine, sodium hydroxide, etc., after the salt has formed. The conversion thereafter is instantaneous.

The process of Example 22 requires temperatures in excess of 110° C., i.e. from 110° C.–180° C., preferably from about 135° C.–150° C. and most preferably at about 140° C. for from about 24–84 hours.

Pharmaceutical compositions comprising a therapeutically effective amount of a compound of the present invention and a pharmaceutically acceptable carrier or diluent are also provided by the present invention.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

I claim:

1. A 1-cycloalkylphosphonium salt represented by the formula

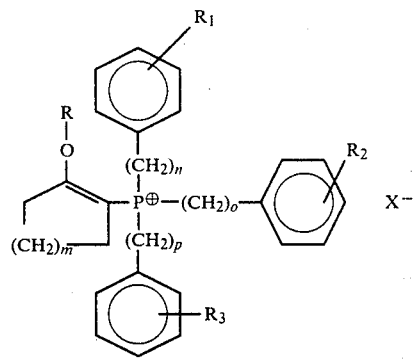

wherein: R is selected from the group consisting of lower alkyl, hydroxy lower alkyl, halo lower alkyl, amino lower alkyl, cyano lower alkyl, lower alkenyl with the limitation that the double bond is not on the carbon atom attached to the oxygen atom, benzyl, substituted benzyl and

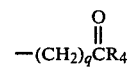

wherein q is 0 or 1 and R$_4$ is selected from the group consisting of hydroxy, loweralkoxy, phenyl, substituted phenyl, and

wherein R$_5$ and R$_6$ are the same or different members of the group consisting of hydrogen and lower alkyl or taken together form a 5 or 6 membered ring; m is 1, 2 or 3; n is 0 or 1; o is 0 or 1; p is 0 or 1; R$_1$, R$_2$ and R$_3$ are the same or different members of the group consisting of hydrogen, lower alkyl, lower alkoxy and halo; and X is a pharmaceutically acceptable anion.

2. A compound of claim 1 wherein m is 1.

3. A compound of claim 2 wherein n, o and p each are 0.

4. A compound of claim 2 or 3 wherein R$_1$, R$_2$ and R$_3$ each are hydrogen.

5. A compound of claim 4: a [2-(phenylmethoxy)-1-cyclopenten-1-yl]triphenylphosphonium pharmaceutically acceptable salt.

6. A compound of claim 4: a [2-(1-methylethoxy)-1-cyclopenten-1-yl]triphenylphosphonium pharmaceutically acceptable salt.

7. A compound of claim 4: a (2-methoxy-1-cyclopenten-1-yl)triphenylphosphonium pharmaceutically acceptable salt.

8. A compound of claim 4: a [2-(3-methyl-2-butenyloxy)-1-cyclopenten-1-yl]triphenylphosphonium pharmaceutically acceptable salt.

9. A compound of claim 4: a [2-(2-oxo-2-phenylethoxy-1-cyclopenten-1-yl]triphenylphosphonium pharmaceutically acceptable salt.

10. A compound of claim 4: a [2-(((2-carboxyphenyl)-carbonyl)oxy)-1-cyclopenten-1-yl]triphenylphosphonium pharmaceutically acceptable salt.

11. A compound of claim 4: a [2-(2-methoxy-2-oxoethoxy)-1-cyclopenten-1-yl]triphenylphosphonium pharmaceutically acceptable salt.

12. A compound of claim 1 wherein m is 2.

13. A compound of claim 12 wherein n, o and p are 0.

14. A compound of claim 12 or 13 wherein $R_1$, $R_2$ and $R_3$ each are hydrogen.

15. A compound of claim 13: a [2-(phenylmethoxy)-1-cyclohexen-1-yl]triphenylphosphonium pharmaceutically acceptable salt.

16. A compound of claim 13: a [2-(1-methylethoxy)-1-cyclohexen-1-yl]triphenylphosphonium pharmaceutically acceptable salt.

17. A compound of claim 13: a (2-methoxy-1-cyclohexen-1-yl)triphenylphosphonium pharmaceutically acceptable salt.

18. A compound of claim 13: a [2-(3-methyl-2-butenyloxy)-1-cyclohexen-1-yl]triphenylphosphonium pharmaceutically acceptable salt.

19. A compound of claim 13: a [2-(2-oxo-2-phenylethoxy)-1-cyclohexen-1-yl]triphenylphosphonium pharmaceutically acceptable salt.

20. A compound of claim 13: a [2-(((2-carboxyphenyl)carbonyl)oxy)-1-cyclohexen-1-yl]triphenylphosphonium pharmaceutically acceptable salt.

21. A compound of claim 13: a [2-(2-methoxy-2-oxoethoxy)-1-cyclohexen-1-yl]triphenylphosphonium pharmaceutically acceptable salt.

22. A compound of claim 1 wherein m is 3.

23. A compound of claim 22 wherein n, o and p each are 0.

24. A compound of claim 22 or 23 wherein $R_1$, $R_2$ and $R_3$ each are hydrogen.

25. A compound of claim 24: a [2-(phenylmethoxy)-1-cyclohepten-1-yl]triphenylphosphonium pharmaceutically acceptable salt.

26. A compound of claim 24: a [2-(1-methylethoxy)-1-cyclohepten-1-yl]triphenylphosphonium pharmaceutically acceptable salt.

27. A compound of claim 24: a [2-methoxy-1-cyclohepten-1-yl]triphenylphosphonium pharmaceutically acceptable salt.

28. A compound of claim 24: a [2-(3-methyl-2-butenyloxy)-1-cyclohepten-1-yl]triphenylphosphonium pharmaceutically acceptable salt.

29. A compound of claim 24: a [2-(2-oxo-2-phenylethoxy-1-cyclohepten-1-yl]triphenylphosphonium pharmaceutically acceptable salt.

30. A compound of claim 24: a [2-(((-2-carboxyphenyl)carbonyl)oxy)-1-cyclohepten-1-yl]triphenylphosphonium pharmaceutically acceptable salt.

31. A compound of claim 24: a [2-(2-methoxy-2-oxoethoxy)-1-cyclohepten-1-yl]triphenylphosphonium pharmaceutically acceptable salt.

32. A pharmaceutical composition having analgesic activity comprising a therapeutically effective amount of a compound of claim 1 and a pharmaceutically acceptable carrier or diluent.

33. A method of treating pain in mammals comprising administering a therapeutically effective amount of a compound of claim 1.

34. A compound of claim 1: a 2-methoxy-1-cyclohepten-1-yl) diphenyl-2-O-methylphenylphosphonium salt.

* * * * *